United States Patent [19]

Reese

[11] Patent Number: 4,979,812

[45] Date of Patent: Dec. 25, 1990

[54] METHOD AND GRAPHICS FOR ACHIEVING OPTIMAL LENS CORRECTION FOR SUBNORMAL VISION DUE TO IMPAIRED RETINAS AND UNDEVELOPED DEFECTIVE FOCUSING ABILITIES

[76] Inventor: Ronald E. Reese, 1500 Locust St., Ste. 2819, Philadelphia, Pa. 19102

[21] Appl. No.: 199,784

[22] Filed: May 27, 1988

[51] Int. Cl.$^5$ .............................................. A61B 3/02
[52] U.S. Cl. .................................. 351/246; 351/203; 351/239; 351/41
[58] Field of Search ................... 351/41, 158, 160, 57, 351/246, 203, 239, 243, 233, 234, 235

[56] References Cited

U.S. PATENT DOCUMENTS

3,027,803 4/1962 Filderman .......................... 351/57 X

*Primary Examiner*—Rodney B. Bovernick
*Attorney, Agent, or Firm*—Penrose Lucas Albright

[57] ABSTRACT

Patients suffering severe retinal damage and focusing impairment are examined in an area having actual or simulated outdoor illumination by viewing a large graphic having colored familiar objects, number and letters of graduated incremental sizes thereon with colored backgrounds either darker or lighter than the objects, numbers and letters involved which the patient points out to ascertain the patient's estimated optimal correction for distance vision. Based on said estimate, the patient is provided with a combination of a soft contact lens either between the estimated correction and a correction obtained by traditional testing methods using black letters against a white background in a darkened room, or the best correction obtained by the examination with the large graphic and a plurality of spectacle type lenses in incremental diopter corrections of two or three diopters for training purposes. The patient trains for a period of about four or more weeks indoors and outdoors whereby the soft contact lenses are worn and the patient views successively through different diopter lenses to improve focusing ability and perception and to arrive at a final optimal correction for soft contact lenses and further spectacle type lenses to be used for reading. During the training period the patient receives supportive therapy which provides detailed information on what the patient should expect and to overcome adverse reactions which may occur incident to the method.

16 Claims, 2 Drawing Sheets

METHOD AND GRAPHICS FOR ACHIEVING OPTIMAL LENS CORRECTION FOR SUBNORMAL VISION DUE TO IMPAIRED RETINAS AND UNDEVELOPED DEFECTIVE FOCUSING ABILITIES

BACKGROUND OF THE INVENTION

This invention relates a procedure to improve visual acuity of individuals having subnormal vision and suffering from significant focusing impairment, usually severe myopia. More particularly, it involves a procedure which includes specially designed graphics for testing visual acuity used for arriving at a best estimate for ocular correction and a prescription for soft contact lenses to be used with a plurality of spectacle lenses for training and eventually determining the patient's optimal correction.

The human eye comprises a lens through which light enters and is focused on nerve endings in the retina to produce a definite mental picture. Muscles direct eyes towards objects to be observed, position their lenses relative to the retina and control the curvature of each lens. The nerve endings of the retina comprise light-sensitive rods and cone cells. Cone cells are responsible for color vision and for detailed vision at the center of the visual field known as the fovea centralis. Although rod cells provide only black and white vision and less detailed information, they are considered much more sensitive at low intensity illumination.

Many people are born with a severe retina damage, having gross scarring, atrophy or irregularities of their retina. Retina damage may be also acquired after birth. In either case, an individual suffering from retina damage may have as little as five to ten percent of his or her operative retina intact in both eyes or in one eye with the other eye worse or completely blind. Such individuals are a challenge to ophthalmologists and optometrists, particularly for ophthalmologists and optometrists who specialize in the treatment of subnormal and low vision patients.

Most patients with low vision are prescribed corrective lenses which are intended to provide the best correction possible at the time of their initial examination. For a number of years, they were taught to "save" their eyes to conserve vision. However they are now advised to use their eyes. Deceptive publicity has occurred from time to time on benefits to be derived from certain optical aids which has had a tendency to give partial seeing patients false hopes. Because of this and because there is no present means known to restore permanently damaged receptors in the retina, patients have been encouraged to live with their handicap and limit their activities accordingly.

It is known that subnormal vision can be corrected in certain instances with contact lenses. However, such improvement has been limited—usually not more than one line of an eye chart. Nevertheless, the degree of magnification in myopia is much greater with contact lenses. It was noted in *Management of the Patient with Subnormal Vision* by G. Fonda published by the C. V. Mosby Company, St. Louis, 1970, that low vision patients do not seem to appreciate the improved visual field contact lenses provide as much as would be expected.

The low vision patient must bring his eyes close to the subject matter to read and for many activities such as eating. For such patient, the outside world is extremely blurred. This contrasts, interestingly, with the patient's ability to see photographs and television images if sufficiently close to same. To test vision between 20/200 and 20/100 special eye charts have been recommended such as the Bausch & Lomb charts 71-35-93 and H-356 and the Sloan letters AOC 11076 project O-Chart. Test types larger than 20/200 have been considered unnecessary because available charts can be used at distances less then twenty feet such as, for example, five feet or less from the patient. A problem with charts in general has been that they are almost always black on white, comprise letters or similar abstract figures and the low vision patient is inclined to make guesses (often accurate) of the letters. It has thus been considered difficult to make accurate eye tests with patients having low vision. Success is often equated with providing the patient with prescriptive lenses which are sufficient to enable him or her to read. This is true although correction of subnormal vision is usually made for both distant and near vision.

There are a number of United States patents which relate to special vision charts and methods of using same for eye exercises. These included U.S. Pat. No. 1,780,291 of Nov. 4, 1930, to A. Cameron which discloses an optical apparatus for testing and charting visual and color fields of a patient's eyes; U.S. Pat. No. 1,990,218 of Feb. 5, 1935, to G. Bailey which is directed to means for determining acuteness of perception on the part of patients for the use of models which may be manipulated; U.S. Pat. No., 2,196,904 of Apr. 9, 1940, to R. Sherman and U.S. Pat. No. 2,387,442 of Oct. 23, 1945, to G. Hamilton relate to devices for testing visual acuity and for visual training which involve the use of stereoscopic devices; U.S. Pat. No. 2,781,042 of Feb. 12, 1957, to J. Bartow discloses a device for testing stereoscopic vision wherein a moving model is employed; U.S. Pat. No. 3,244,468 of Apr. 5, 1968 to R. Meltzner discloses a diorama which is used for testing visual acuity with three dimensional scenic representations; U.S. Pat. No. 3,842,822 of Oct. 22, 1974 and U.S. Pat. No. 3,955,565, of May 11, 1976 to H. Levinson et. al. relate to dysmetric dyslexia screening procedures and method of improving ocular fixation, sequential scanning and reading activity in dysmetric dyslexic children; U.S. Pat. No. 3,910,690 of D. Regan of Oct. 7, 1975, relates to apparatus for measuring visual acuities in different retinal areas of the patient; U.S. Pat. No. 3,986,500 to H. Tsuruta of Oct. 19, 1976, discloses therapeutic treatment for myopia by a repetition of focusing and staring alternatively at a distant object and a nearby object and a visual acuity chart; U.S. Pat. No. 4,365,873 to A. Ginsburg of Dec. 28, 1982, which discloses a visual chart and method of using same to evaluate the visual and optical systems of patients undergoing analysis in terms of both contrast sensitivity and spatial frequency response.

SUMMARY OF THE INVENTION

There is a high correlation that a patient with severe retina damage also suffers from abnormally elongated eyeball which produces a severe myopia. This may be due to a decreased capillary blood pressure in the damaged retina compared with a normal eye which weakens its surface strength and increases the likelihood of some degree of wall collapse. It is also believed that the lenses of the eyes of patients suffering from severe retina damage tend to be more thickened than usual partly because they attempt to achieve better focus on their abnormally distant retinas and, to ensure a greater population of their live receptors receive the image, they tend to bring everything closer to their eyes.

Thus, for the myopic patient with severe retina damage, the only effective vision is near vision and the patient is not trained, so to speak, in the constant focusing of the eyes for near and far vision which exists in individuals having normal vision. Nystagmus can also be a problem. Low vision patients need considerable time to integrate what they can see and this time-lag is a definite disadvantage when they are undergoing visual tests.

It is theorized that because of the above circumstances the low vision patient has frequently not learned to use the focusing mechanisms of his eyes to the best advantage and also is not employing what receptors he does have in the damaged retina efficiently. The need is therefore to teach the low vision patient to focus the maximum amount of light energy on the available receptors and to utilize for perception all the receptors receiving the image.

To improve the vision of the high myopic patient having severe retina damage, the first step of the instant invention is to estimate the correction needed for optimal correction of distant vision in the everyday world. Because with the present state of the art such correction is an estimate of the optimal correction rather than an actual optimal correction, it is referred to herein as a reified or reification optical correction; that is, it is an abstraction considered initially as reality. The actual correction cannot be known with certainty until the patient has undergone a procedure which will be described in more detail and which both trains and assists the patient and enables the specialist to ascertain the best correction, after the eye's muscles used for focusing and the brain are better coordinated and adept to receive and process images received by the severely damaged retina. This is accomplished by prescribing for the patient a lens having a strength about midway between the estimated optimal correction or reified correction and the correction previously obtained by conventional means, if made. This further correction is then used to obtain soft contact lenses to be used in combination with further spectacle type lenses for optimal distance vision. The patient also learns at the same time a best reading correction for spectacles to be used with the contact lenses.

A highly structured and disciplined cooperative effort must be established almost immediately between the ophthalmologist or optometrist on one hand and patients on the other hand which fixes in each patient's mind that he or she must accurately communicate to the doctor exactly what he or she experiences visually in the testing and training phase of the invention. It must be appreciated that an important aspect of the process is for the patient, in effect, to learn how to learn how to see and a positive attitude is imperative.

For a patient who has suffered from low vision from birth, the experience is similar to an infant learning to see. This experience for a grown adult can be traumatic. For patients who can benefit from the instant invention, their visual improvement is marked, but not without definite limitations. Moreover, their world becomes considerably more complicated and unfamiliar. Working against strong motivations for improved sight, are deep seated reactions in many patients to reject the intense, more complex world which they are experiencing. On the other hand, there may be unrealistic expectations for improvement beyond that possible in view of their physical limitations. It is important that the practitioner expect, recognize and manage, these mental reactions as necessary.

In other words, improvements in visual acuity both for distance and for reading of patients who undergo the method of the invention are sufficiently dramatic that the practitioner should at all times be aware not only of the need for continuing visual education and training exercises to achieve optimal vision over a period of time, but also of the need for an on-going supportive psychotherapy to reinforce advances patients are making in visual acuity and to minimize effects of certain resistance, fears and the like which may attend the procedures described herein.

The primary purpose of the instant invention is to achieve the foregoing improvements in visual acuity in patients suffering from severe retinal damage and focusing impairments, usually myopia. However, other objects, adoptabilities and capabilities of the invention will be appreciated by those skilled in the art as the description progresses, reference being had to the accompanying drawings.

BRIEF DESCRIPTION OF THE DRAWING

FIGS. 1 and 2 submitted herein are graphics which, although in black and white for the purpose of being reproduced in the patent document, are, in fact, entirely in color. The graphics are for use by the ophthalmologist or optometrist to ascertain whether or not a patient can be improved by the method of the instant invention and, if so, to determine the estimated optimal correction the patient can achieve. The graphics are also used by patients for training purposes. Each is about fifty by fifty inches and provides in contrasting colors, letters, numerals and familiar figures of various objects in light against dark and dark against light backgrounds to be identified by patients in initial and subsequent testing as will be described hereinafter.

DESCRIPTION OF THE PREFERRED EMBODIMENTS

Figure 1:
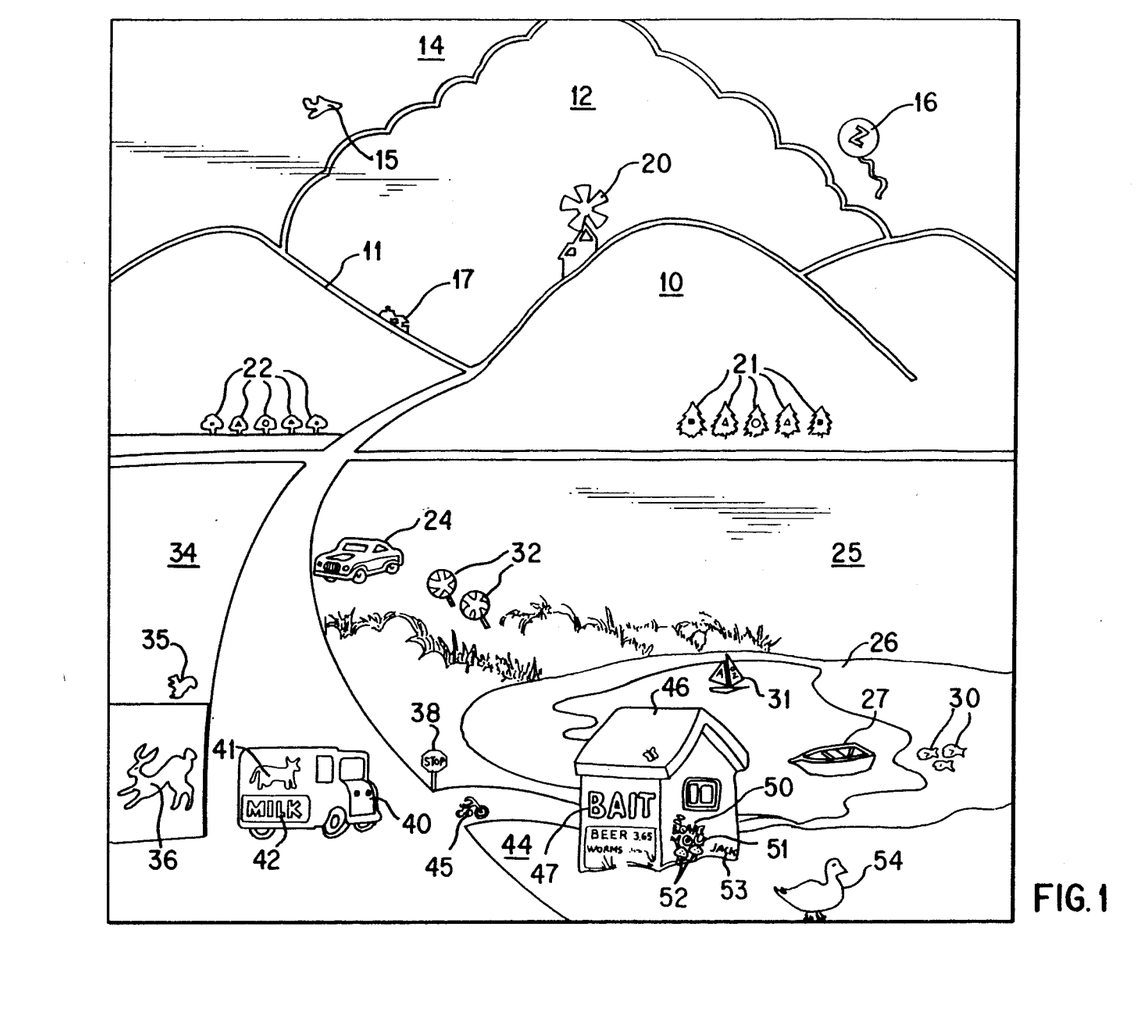

Reference is now made to FIG. 1, a graphic to be used as an "eye chart" for the ophthalmologist or optometrist to ascertain the patient's estimated optimal correction for soft contact lenses and subsequently for the patient's use in the practice of procedures and methods disclosed herein.

FIG. 1 is a graphic which shows a scene having hills 10 and 11 in the background against a cloud 12 in a sky 14 in which is an airplane 15 and a balloon 16 with a string and a Z thereon. Over the hill 11 is a house 17 and on the other side of hill 10 is a windmill 20. In the foreground of hill 10 are five pine trees 21 which have in them a small square, triangle, "O", another triangle and another square respectively. At the edge of hill 11 are five further similar trees 22 which may be willow or "umbrella" trees and which also have outlined therein a square, triangle, a circle, another triangle and another square respectively. In the foreground of the FIG. 1 graphic is a field 25 which has a pond 26 containing a row boat 27, fish 30 and a sailboat 31 having an "A", "O" and "Z" on its sails. In field 25 above pond 26 are two beach-type umbrellas 32. There is on the left a further field 34 which becomes darker in the foreground and has a squirrel 35 in the lighter part and a rabbit 36 in the darker part.

Between fields 25 and 34 is a road 37 on which is a milk truck 40 having painted on its side a cow 41, branded with an "arrowed B", and the letters "MILK" 42. A lane 44 leads from road 37 to pond 26 and has thereon a tricycle 45 near a stop sign 38. In front of lane 44 is a bait house 46 having "BAIT" in large letters 47 on one side and "I LOVE" 50 in one size of letters with "YOU" 51 in larger letters and "JACK" 53 in smaller letters. Two mushrooms 52 are in front of the bait house. A duck 54 is in the foreground.

Sky 14 is a deep blue compared to a light blue for cloud 12. Windmill 20 is brown or tan as compared to a dark brown for house 17. Hill 11 is green and the same color as trees 21. By the same token, hill 10 and field 34 are the same color as are field 25 and trees 22. The blues of the sky 14 and cloud 12 are repeated in the darker and lighter portions of pond 26. Balloon 16 is yellow and the "Z" thereon is red. The same red is applied to rowboat 27. The road 37 is a faint blue—considerably lighter than cloud 12. Squirrel 35 and the background for rabbit 36 are the same brown color as windmill 20. Automobile 24 is outlined in the same red as for rowboat 27 and the "Z" in balloon 16 as well as stop sign 38. Umbrellas 32 have strips which are a light yellow-green. Tricycle 45 has a red frame, brown wheels and a darker brown seat. Milk wagon 40 has a background of blue for cow 41, the same blue for the lettering "MILK" 42, a red door front part and hubcaps and dark brown wheels. The bait house is a dark brown and dark yellow with red lettering on the front and "BAIT" is in dark yellow, the roof being a faint yellow. Sailboat 31 is of the same color as the road 37. Duck 54 is orange with brown feet.

It will be recognized that numerous figures and the lettering are each depicted in either a dark color against a light color or vice versa. The following is a chart to be used by the practitioner in obtaining the patient's best estimated corrections using the graphic shown in the FIG. 1:

| DARK BACKGROUND | | LIGHT BACKGROUND | |
|---|---|---|---|
| | | 20/400 | Bait House |
| | | 20/200 | Milk Truck |
| 20/150 | Jack Rabbit | 20/150 | Windmill |
| 20/100 | Balloon | 20/100 | Duck |
| | Sailboat | | Automobile |
| 20/70 | Cow | 20/70 | Row Boat |
| | Beach Umbrellas | | Pine Trees |
| | | | Cliff House |
| | | | Squirrel |
| 20/50 | Willow Trees | 20/50 | Z (Balloon) |
| | | | Stop Sign |
| | | | "MILK" |
| 20/40 | Mushrooms | 20/40 | Tricycle |
| 20/30 | Airplane | 20/30 | Tricycle Front Wheel |
| | | 20/25 | "YOU" |
| 20/20 | Three Fish | 20/20 | "I LOVE" |
| | "STOP" | | "A" (Sailboat) |
| | "O" (Pine Tree) | | "O" (Willow Tree) |
| 20/15 | Triangles (Pine Trees) | 20/15 | "JACK" |
| | | | "OZ" (Sailboat) |
| | | | Triangles (Willow Trees) |
| 20/10 | Squares (Pine Trees) | 20/10 | Arrow-B Brand on Cow |
| | | | Square (Willow Trees) |

The purpose of the FIG. 1 graphic is to provide a real-life context for vision testing purposes as opposed to the usual isolated letter symbols. In addition, the use of color and proper illumination therewith (both fluorescent and incandescent sources used together), simulate daylight conditions thus activating the cones of the retina to provide the sharpest central vision. This permits, insofar as possible, all of the live receptors of the retina to come into play during the examination. Both the objects and the numeral and letter symbols are in contrasting color and precisely employ the graduated sizes of standard eye charts.

In practicing the method in accordance with the invention, the ophthalmologist or optometrist first determines whether or not the patient can accept soft contact lenses. For most, if not all, patients who can benefit by the method described herein, prescriptions in ordinary spectacles for the corrections needed prove too thick to be practicable and therefore their acceptance of soft contact lenses is imperative.

When it is determined that a patient is capable of accepting soft contact lenses, an eye examination is given to provide an estimate of the patient's optimal distant vision correction with such lenses. It is assumed that the patient already has an existing correction either for contact lenses or spectacles. If not, a conventional visual acuity examination is given to determine, at least roughly, the correction which would be prescribed using conventional eyesight procedures for the low vision patient. Thus before the initial examination step, the ophthalmologist or the optometrist ascertains whether or not the patient can tolerate soft contact lenses and learns either exactly or roughly the patient's best correction using conventional methods. With this information, the patient is tested in a well-lighted room (having both fluorescent and incandescent lighting or other means for simulating daylight conditions) with the graphic shown in FIG. 1 and objects in the room.

It is important at this point the patient be instructed not to guess at an object but to report to the person conducting the test only crisp clarity of line and increasing vividness of color. If a distance of five feet or ten feet is too far for the patient to experience clarity with certainty, he or she should have the relative distance to the graphic reduced so that the patient knows what is wanted. Once this is understood, then the patient can provide the necessary information for an estimated optimal correction. The patient's examination should not be hurried and the patient should be provided sufficient time to focus on the graphic and also selected distance articles in the examining room.

For the myopic patient, starting with minus diopter lenses, the minus diopter is increased successively until distant objects become so small that further increase in clarity is negligible value or until the environment commences to blur.

Once the estimate of optimal distant vision is determined, it is recorded as the patient's "reification correction for distant vision." A prescription is then made for a soft contact for each eye at about midway between the reification correction for distant vision and the correction obtained by conventional methods. Soft contact lenses at such corrections are used by the patient for a period of roughly twelve weeks while he or she undergoes training for outdoor distant vision and also for reading with spectacles or using spectacle type lenses with plus and minus diopters of different strengths, which are in about two or three diopter increments as appropriate, and which can be tolerated with the soft contact lenses.

The next step may be accomplished by the patient without constant supervision although continued monitoring and support should be considered requisite. During this period, the patient practices, wearing the prescribed soft contact lenses with various spectacles, seeing at various distances, and also reading. Practice is both indoors and outside and its purpose is twofold. The first is for the patient to determine which of the corrective spectacles are best for him or her. This may, and probably will, change until a plateau of best corrected vision is obtained. The second reason is to provide the patient with focusing practice which involves use of the muscles of the eye in a coordinated motor relationship with the part of the brain which provides perception to the patient. For the patient who has had low vision since birth, the process is a learning one experienced by the patient for the first time and may be attended by reactions similar to headaches which the inventor ascribes to reactions of the muscles used in focusing and the patient's initial use of heretofore unstimulated and dormant brain pathways for processing the visual signals in the brain. Such symptoms, however, are considered a positive sign of stress and not unnatural in an ongoing learning process.

It is questionable that the second step should be initiated for patients who failed to display initial positive attitudes towards taking this step. An initial failure of an overly dependent or neurotically touch-sensitive patient may cause subsequent psychological rejection of the method at a time when the patient might otherwise be better motivated.

During the training period, the patient, in effect, reaches his own correction by adding minus lenses to obtain optimal distance correction and adding plus lenses to correct for reading. Supervision and support is provided which emphasizes the importance of selective distance focusing on a daily basis. Consultations at the office are arranged during this period. The patient is encouraged to experiment and in training to use successively increased diopter strength lenses.

For the patient with severely damaged retinas, the initial subjective difference experienced from lenses one or two diopters apart is minimal. It is important that the communication gap between the patient with retinal damage who has never known what it is to see well and that of the practitioner who has never experienced vision with severe retinal damage be narrowed insofar as possible. Improvement may be dramatic, albeit by stages, until finally the patient reaches a plateau of optimal vision and, at such correction, the patient's final minus diopter soft lenses are prescribed with the appropriate plus diopter spectacles for reading glasses. Protective safety glass sunsensor glasses are suggested for outdoor use. It has been found soft contact lenses of the lenticular design are preferable because they afford a larger optical center than stock lenses. However, such lenses being somewhat thicker at the edges, may be more difficult for the patient to tolerate. Nevertheless, the large optical center of the custom made lenses provides improved vision with a minimal and tolerable loss of comfort.

Follow-up visits should, of course, be scheduled to ensure the best optimal correction has been made.

As an example of the above method, a patient who is blind in one eye and has between five and ten percent live receptors in the other eye was prescribed a minus 14.50 diopter correction by conventional tests. His initial reification correction for estimated distance vision was minus 27 diopters. His training correction was minus 21.50 diopters. For reading with the minus 21.50 training lens, he required a plus 8 diopter spectacle. However, he could read and see more clearly at longer distances from his eyes, six to eight inches from the material, compared with the distance using his traditional correction, minus 14.50 diopters, of two to four inches. With a minus 5.50 diopter spectacles used with his 21.50 training lens he was able to see much better than ever. Bus numbers were clearer, colors were richer, texture was more present that previously. With an increase of minus 8 diopters further improvement occurred; automobiles could be seen from further away. For the first time, he was able to see salt coming out of a shaker at normal sitting distance.

Each time the patient increased the power, he began to have "headaches" and feared he might be stressing his eyes too much, hurting them without realizing it. However, the headaches soon disappeared. In addition, he experienced soreness and "headaches" to the eye muscles. He increased the minus diopter of training spectacles by degrees until a minus 31.50 diopter correction was determined to be the best. The patient, who had been highly motivated by the increasing visual perception, experienced disappointment when it was realized that optimal correction had been achieved and further improvement was unlikely.

The patient, although still a severely disabled individual, can now at twenty feet see salt and pepper shakers well enough to identify them. He can see a napkin holder, faces well enough to determine if one is wearing glasses or has a mustache at the same distance. With his traditional prescription he could at best make out these distinctions at between two and three feet.

His night vision improved less but still is considerably improved. Before optimal correction, predominately black and white features of the visual field at night faded into obscurity beyond two or three feet. However, now at least five to ten times clearer distance perception at night is possible. The patient experiences some double images at the edges of the optical portion of his soft lens when a bright light source hits its thick edge. He had previously suffered from chronic nystagmus—the involuntary jumping of the eye—which has virtually disappeared. Reading is continued with plus 8 diopter reading glasses although a plus 12 diopter hand-held magnifier is useful for him at times. He reads faster with more clarity and with a greater visual field even under magnification than previously, the material being held at about ten to twelve inches from his eyes. The patient experiences considerably more confidence at traffic crossings and can see automobiles and even bicycles at eighty to one hundred feet away.

The patient is still legally blind. Uncorrected, his eye tests at 20/800 which could be traditionally corrected to 20/400. Using a traditional eye chart in a darkened room, with his new soft contact lens, correction remains at 20/400 at twenty feet. This is because his eye cannot integrate the thin black lines or letters at twenty feet. However, at five feet, using the traditional chart, the patient now has a 20/280 visual acuity converted from 5/70. At five feet with the colored graphic of the drawing, he has a visual acuity of 20/200 dark on light ground (5/50 converted) and 20/160 visual acuity with light on dark background (5/40 converted). The patient's improvement, however, for ordinary functioning is more dramatic than the examinations would indicate. He can see a school bus clearly at one hundred feet instead of less than ten feet before and he recognizes the faces of colleagues at the end of a twenty foot conference table instead of at his previous limit of two feet. It is difficult for others to perceive him except as virtually normal, a fact which has greatly enhanced his self-image and self-esteem.

A second patient has suffered from massive retina damage since childhood. She had been examined by a number of ophthalmologists and optometrists who informed her that her case was hopeless and she was never prescribed corrective lenses. Unlike the first patient, she has binocular vision. Her retina damage is massive and primarily in the fovea centralis of both eyes. In addition to moderate myopia, she suffers from astigmatism in both eyes.

For training purposes she was prescribed minus 3.5 diopter with appropriate axes deviations. Her vision increased in distance perception by over ten times in a two and one-half month period of training by the above invention. She can now read at eight to ten inches whereas she could not read at all previously. There was a remarkable improvement not only in her vision but also in social functioning. In contrast to the first patient, her night vision has increased even more markedly than her daytime vision undoubtedly due to the disproportionate percentage of rod receptors remaining in her eyes. The anticipated optimal correction of this patient is a minus 5 diopters in each eye with appropriate axes deviations. The visual restoration afforded this patient, considered hopeless for the first fifty-six years of her life, has been truly remarkable and has been advanced by optimal stimulation of her remaining receptors in conformity with the instant invention.

The instant invention has application to individuals suffering from focusing difficulties of a severe type whereby their corrected vision is 20/100 or worse and also have retina damage of various magnitudes. Improvement is increasingly significant the greater the retina damage assuming, of course, a reasonable number of live receptors remain. This invention has no application to those patients already capable of focusing their eyes or where the retina damage is so severe that significant live receptors to provide visual images are not present.

There are three parts of the method disclosed. These comprise first the proper optometric evaluation and prescription utilizing the color graphic and identifying patients suitable for treatment in accordance with the invention; second the vision education and training exercise phase whereby the patient is taught how to exercise in selective distance focusing and to apply a daily regimen of vision training exercises to ensure optimal correction in the shortest possible period with minimal difficulty; and third psychotherapy support to assist each patient in understanding what to expect and supporting the patients to minimize psychological problems precipitated by their new experiences. Where possible, the latter should be accomplished by a training psychologist providing therapy in support groups and individually.

The psychologist in group sessions educates patients concerning the human eye, its parts, lens function, retina functions, differences of rods and cones, and generally how information is transferred to the brain, understood and responses are initiated. The visual learning process is explained to patients both in a general manner and as applied uniquely to each individual case.

In this training phase, the practitioner must keep in mind that the chronic use of near vision has effectively prevented the patients from learning to focus on targeted distant objects and hence they have never learned to experience their extended environment. The undercorrected or noncorrected myopic individual may be an adult physically. However, in terms of vision education, he or she is literally similar to an infant who is just beginning to learn focus on, make sense of and respond to his or her extended world. This is a deficit vision function which can be corrected only by regularly practiced selective distance focusing. More specifically, each patient is instructed to practice for at least thirty minutes twice a day for vision training purposes. Although this may commence before the soft contact lenses for training are obtained, significant improvement should not be expected until the training lenses are used. The patient is instructed to hold the head steady and let the eyes move side to side and up and down seeking increasingly smaller objects and more distant objects in the environment. The patient maintains focus of each object for at least ten seconds and then focuses on a closer object which is more relaxing to the patient, subsequently, the patient is instructed systematically to direct his or her line of sight at the twelve o'clock positions, relax, and repeat same from the one o'clock to the seven o'clock positions, the two o'clock to the eight o'clock positions, the four o'clock to the ten o'clock positions, and the five o'clock to the eleven o'clock positions. At all times, the head is held still and in each instance the patient attempts to concentrate, focus and hold his or her sight on the various selected size objects and distances. The same steps are applied for at least thirty minutes twice a day during daylight hours. About fifteen minutes may be indoors in a well illuminated room and the remaining fifteen minutes should be outside. When the patient has progressed sufficiently with these exercises, he or she should be encouraged to do the exercises while walking, riding or otherwise moving. The goal is for the patient to respond to the extended environment as fully as possible. The patient is normally given considerable latitude to experiment with different spectacle lenses, but encouraged to increase the strength in successive exercises and as the training period progresses.

Each patient is strongly encouraged to maintain a journal of progress made and to set forth in same, in the manner of recording experiences in a diary, his or her feelings, particular experiences, and his or her fears or hopes concerning the visual experiences. These are useful for weekly therapy groups.

The goal emphasized to each patient is to discover where his or her live receptors are and to learn to use them as fully as possible in everyday activities. The ultimate goal is to achieve insofar as possible a sense of normalcy as perceived by the normally sighted.

The need for continuing psychotherapy cannot be overemphasized. Patients should not expect steady improvement but rather periods of improvement in stages with intervening plateaus. These individuals are not likely to have closely or nearly the same vision impairments and capacities but rather significantly different ones. Thus each person must be made to understand that his or her vision correction problems are unique. The psychologist provides a catharsis for the patient to unload deep-seated emotions connected with his or her defective vision. This enhances honesty and spontaneity in practicing the method disclosed here. Negative attitudes are to be avoided and changed insofar as possible to affirmative, positive attitudes. Vision exercises should be reinforced by the psychologist until the vision skills obtained become spontaneous. Eventually the psychologist should ensure that the patient has a realistic understanding of his or her disability and possibilities of vision improvement. Possible new vocational or employment opportunities once optimal correction is achieved should be assessed individually.

For maximum fulfillment of the method for patients considered individually the process should be viewed as interdisciplinary requiring the coordinated efforts of the ophthalmologist or optometrist and a therapist who will usually be a psychologist but in limited instances a psychiatrist.

From the foregoing, it will be understood that the method and procedures described above provide substantially increased practical vision for the patients at prescriptions considerably different from those initially made. It is considered this is possible due to the availability of prescription soft contact lenses, the testing method and training described above, improved communications between patients and practitioners, and eventually the final prescriptions.

The method constitutes a precise learning process coordinated with the FIG. 1 graphic or a similar "eye chart" to standardize and verify the patient's changes in visual acuity over a period of time. Without subjectively refined feedback from the patient to the ophthalmologist or optometrist, it is difficult to achieve both the optimal prescription and adaptation by the patient in practicing the method disclosed herein.

Improved visual acuity achieved by the patient in the period required for the treatment set forth above is not necessarily the ultimate best vision which the patient may achieve. Additional refinements and improvements in acuity may be attained thereafter. The optometrist and ophthalmologist for the patient whose visual acuity has been improved by the methods disclosed herein should not hesitate, even after a period of several years, to investigate whether or not further prescription changes may further improve the visual acuity of the patient. In the first example described above of a patient whose best correction was determined to be a minus 31.5 diopters, recent testing and experimentation has established that sharper and more vivid detail is obtained with a minus 34 diopter soft lens correction. With same, reading has been moderately improved and distance vision is about ten percent greater than before. This increased acuity could not be obtained approximately two years earlier when the minus 31.50 diopter correction was determined to be optimal and corrections greater than 31.50 diopters definitely reduced the patient's visual acuity. It is a reasonable hypothesis that this increased visual acuity developed due to the daily "practice" by the patient in the intervening period or, in other words, the coordination between the patient's focusing ability and use of his remaining active retina has improved as a result of the increased use of his vision in the everyday world.

Once a patient attains, by using the method of the instant invention, optimal visual acuity, his or her confidence is substantially improved. Important for this result are the patient's improvements in the reaction time which, in turn, greatly increases his or her personal safety at traffic crossings and in the home. Moreover, real and phobic anxieties and fears of the patients are substantially reduced in such situations. Patient's capacities to function in the everyday world are thus increased by an order of magnitude and this is reflected in their improved self-esteem and social interactions. Their internal personal psychological changes in sense of self worth and freedom from fears are the most marked improvements. These are significantly greater than might be anticipated from the visual acuity changes, per se. Increased employment possibilities are probably the most important outgrowth of the invention.

It was considered that the graphic disclosed herein in FIG. 1 might serve better than traditional eye charts to arrive at the proper correction for soft contact lenses of persons who do not have retina damage but who suffer from undeveloped defective focusing abilities. Two patients, "S" and "K", both suffer from severe nearsightedness in one or both eyes. They were tested by the FIG. 1 graphic in a surrounding well lighted colorful environment in substantially an identical fashion as for patients having severe retina damage. As a result, both patients achieved at least one line improvement by traditional examination eye test and each reported less eye strain with close work, the absence of tension headaches previously experienced as a result of close work over an extended period of time, greater overall visual clarity and an improved sense of vividness in form and color in their ability to see and perceive objects at a distance. Their visual changes are indicated in the following table:

| Patient | Uncorrected Acuity | Correction Achieved By Traditional Testing Methods | Correction Achieved By Method Of Invention |
|---|---|---|---|
| S, 31 year old nearsighted astigmatic, no retina damage | R = 20/400<br>L = 20/30 | R = 20/40<br>L = 20/25 | R = 20/20<br>L = 20/20 |
| K, 27 years old, severe nearsightedness, both eyes, astigmatic, no retina damage | R = 20/400<br>L = 20/400 | R = 20/40<br>L = 20/50 | R = 20/25<br>L = 20/40 |

All of the above corrections were made with soft contact lenses and a prescription for patient S was minus 2.5 diopters for the right eye and minus .50 for the left eye with appropriate axes deviations for astigmatism.
For patient K the prescription lenses were right minus 8.5 diopters and left minus 7.25 diopters, again with appropriate axes deviations for astigmatism.

Both patients S and K required much less instruction and training due to their undamaged retinas as compared to severely impaired patients with retina damage and a lifetime of visual poverty. Nevertheless, their improved visual acuities are regarded significant and unique.

Subsequent to the foregoing, a research project was commenced and completed using thirty-four patients for whom complete results were recorded. It was found that:

1. Functional visual acuity (distance vision) was radically improved from two to seven times in every case—fully treated or in some phase of treatment.

2. Errors in final refractions by traditional methods ranged from 40% to 340%. Forty percent error or more was found to exist in more than forty screening examinations. When compared with traditional, conventional low vision correction methods, average discovered error in prescriptions was greater than 100%.

3. Disease origin was not a factor, with the possible exception of retinitis pigmentosa. Fourteen different origins were successfully treated, including macular degeneration and diabetic retinopathy.

4. Age was not a factor—range=17 to 73.

5. Excellent neutralization, when examined by the retinoscopy, was achieved in nine out of ten cases. The other one of ten showed good signs of neutralization. (The literature on low vision correction is replete with assertions that good neutralization is difficult to impossible in such cases.)

6. Nystagmoid movement (involuntary jumping of the eyes) was radically reduced or eliminated in every case.

7. Reading speed and ease improved in every case.

8. A radical reduction in phobic fear (panic state) in dealing with unfamiliar environments and environmental conditions such as traffic was achieved in every case.

9. Radical improvement in eye contact was achieved in every case.

10. Radical improvement in self-esteem, spontaneity, and grooming habits occurred in all cases (not induced or suggested by the professionals conducting the clinical study).

11. Significant reduction or elimination of "blindisms" occurred in all cases. ("Blindisms" are abnormal behaviors resulting from low vision patients' relative inability to imitate the behavior of normally sighted individuals.)

12. As seen by normally sighted persons, patients appeared to be significantly more "normal" and independent socially, i.e. much less handicapped.

13. The data tabulated suggested that a 95% confidence level can be achieved. (A 0.05 level of significance was confirmed by statistical analysis.)

14. Only two of the cases examined were deemed unsuitable for treatment. Hence, preliminary indications were that more than 90% of the partially sighted population will be treatable.

All of the above findings were substantiated by cross-validated objective ratings by (1) self, (2) other family members, (3) cross validation of instruments, (4) doctor and staff, and (5) retinoscopy.

Figure 2:
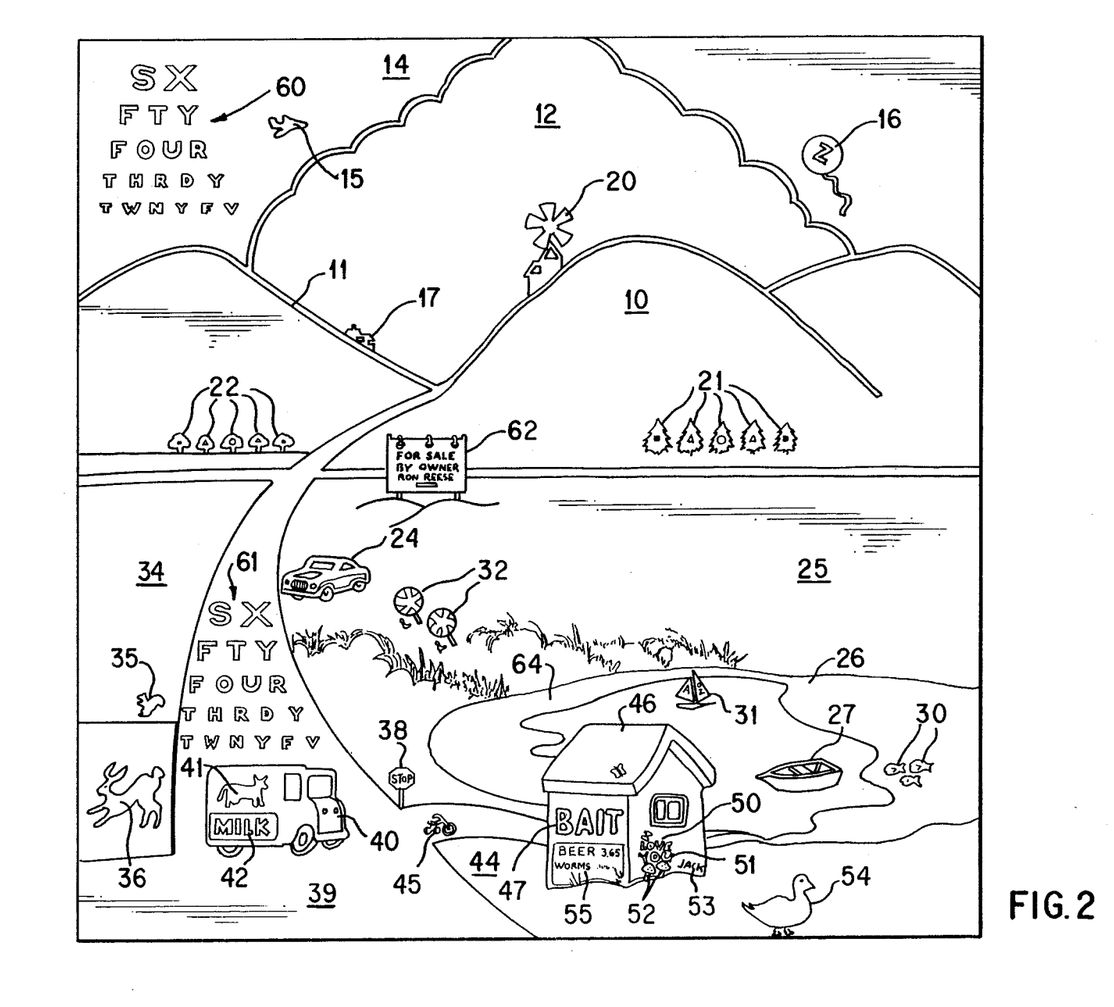

FIG. 2 is a further graphic which was developed for research which contains the same elements as the FIG. 1 graphic with certain additional elements. These included a sign 55 on the baithouse, lettering 60 in the sky and 61 on the road, a for sale sign 62 in the background and a small white swan 64. The lettering 60 and 61 was to identify the value of reverse contrast for each patient. This knowledge can be applied in their every day life environment for more "normal" functioning. For example, an individual might find that having a dark colored kitchen table top or counter would enhance his or her ability to discriminate lighter objects on the table or counter.

The following table sets forth the significance of symbols in terms of functional visual acuity for the FIG. 2 color graphic eye chart.

| "Significance of Symbols in Terms of Functional Visual Acuity" FIG. 2 Chart | | | | |
|---|---|---|---|---|
| Snellen Percept Equivalent at 20 Feet | Dark Background | Light Background | Visual Acuity at 5 Feet | Visual Acuity at 10 Feet |
| 20/400 | | Bait House | 20/1600 5/400 | 10/800 10/400 |
| 20/200 | | Milk Truck | 20/800 5/200 | 20/400 10/200 |
| 20/150 | Jack Rabbit | Windmill Billboard | 20/600 5/150 | 20/300 10/150 |
| 20/100 | Balloon Sailboat | Duck Auto | 20/400 5/100 | 20/200 10/100 |
| 20/70 | Cow Beach Umbrellas Airplane "Bait" on Baithouse | Rowboat Pine Tree Cliff House Squirrel | 20/280 5/70 | 20/140 10/70 |
| 20/60 | "S, X" | "S, X" | 20/240 5/60 | 20/120 10/60 |
| 20/50 | "F, T, Y" Willow Trees | "F, T, Y" "Milk" "Z" | 20/200 5/50 NOTE: | 20/100 10/50 Stop Sign |
| 20/40 | "F, O, U, R" Mushrooms | "F, O, U, R" Tricycle | 20/160 5/40 | 20/80 10/40 |
| 20/30 | "T, H, R, D, Y" Spotlights | "T, H, R, D, Y" Beach Chairs Front Wheel of Tricycle | 20/120 5/30 | 20/60 10/30 |
| 20/25 | "T, W, N, Y, F, V" Swan | "T, W, N, Y, F, V" "You" Butterfly | 20/100 5/25 | 20/50 10/25 |
| 20/20 | "For Sale" Three Fish "Stop" "O" (Pine Tree) | "Beer" "I Love" "A" (Sailboat) "O" (Willow Tree) | 20/80 5/20 | 20/40 10/20 |
| 20/15 | "By Owner" Triangles (Pine Tree) | "3.65" "Jack" "OZ"(Sailboat) Triangles (Willow Trees) | 20/60 5/15 | 20/30 10/15 |
| 20/10 | "Ron Reese" Squares (Pine Trees) Window (Cliff House) | "Worms" Squares (Willow Trees) Arrow B Brand (Cow) | 20/40 5/10 | 20/20 10/10 |

-continued

| "Significance of Symbols in Terms of Functional Visual Acuity" FIG. 2 Chart | | | | |
|---|---|---|---|---|
| Snellen Percept Equivalent at 20 Feet | Dark Background | Light Background | Visual Acuity at 5 Feet | Visual Acuity at 10 Feet |
| 20/5 | | "59¢/Doz," | 20/20 | 20/10 |
| | | "S.O.S." (Row Boat) | 5/5 | 10/5 |

NOTE:
The following symbols are painted so that "Black light" illumination can be used as an added technique in determining whether low vision patients respond best to reverse contrast, i.e., "light on dark." In assessing needs for best reading adaptation, this technique can reveal and confirm important information in individual cases.
Plane - yellow
Balloon - yellow and orange
Stop Sign - orange
Butterfly - blue and orange
"Bait" on Baithouse - yellow
Lights on Billboard - orange and yellow
Symbols in Pine Trees - yellow
Stripes on Umbrellas - green
Auto - orange and blue
Window in Cliff House - yellow The reason for the FIG. 2 eye chart was to provide a greater number and variety of unpredictable symbols and objects in the chart for diagnostic purposes. As the practitioner instructs the patient to tell him everything the patient can see, he simply circles each correctly reported object on a form such as the above chart.

In the clinical study it was learned that in most cases the correct prescription required for optimal vision was apparently determined reasonably accurately as a result of the patient's first test of the eye chart. What the patient considered to be his or her best corrections with each eye were selected to be the training lenses. Neutralization by retinoscopy was good to excellent in all cases. In many cases, it was found that the initial prescription for optimal vision was the same one settled on after a ninety day training/learning period.

However, in every case of the clinical study, the training prescriptions and the prescriptions for optimal vision were different than those which had been previously prescribed to the patients by conventional methods. The lowest lens change recorded was 10% in one eye. With this particular patient, that 10% change plus a greater correction in the more damaged eye, remarkably improved the patient's binocular vision as well as social mobility and normalcy. Based on experience from the clinical study, it is believed the early radical and positive changes in prescription and in the seeing ability demonstrated by the patients was achieved due to the uniqueness of the graphic. In this respect, it will be appreciated that the patient is normally the usual five feet or sometimes less distance from the chart and the chart itself is four feet by four feet which provides an area of sixteen square feet. Thus the patient is forced by the size of the graphic to search both horizontally and vertically to seek and identify increasingly smaller symbols/numbers/letters. It is considered that this forced range of movements favorably affects the learning process. It has, on the basis of experience, been concluded that there are three conditions necessary for optimal developmental vision and focusing abilities to be achieved by the patients. These conditions are; (1) unlimited eye movement (2) an unpredictable visual stimulus; and (3) a secondary motor commitment involving eye-hand, foot, head involvement.

The patient is instructed to feel free to move his or her head from side to side along the five foot line or to roll a wheel mounted chair from side to side. The patient is also required by the practitioner to point at the symbol or letter identified using a baton with an extended arm or, alternatively, to point with a bright pencil flashlight. Using a pencil flashlight, when the patient identifies a symbol, letter or word, he or she is requested to use the pencil flashlight for illuminating the object, letter or word and inform the practitioner precisely what he or she sees. It has been found that this strategy requires the patient to get his or her entire body involved and this, in turn, seems to accelerate the learning process. It will be appreciated that this method contrasts with traditional methods and charts which do not force the necessary movement for secondary motor commitments. In general, conventional eyecharts are too small and/or are located too far away. They thus only use or emphasize central vision. This may contribute to their failure to provide an optimal prescription for distance and mobility.

It has been found important that before the examination and learning experience is commenced, certain specific techniques by the practitioner at the beginning of the examination are virtually a requisite to ensure best results. The instructions are, in a sense both psychotherapeutic and educational in nature. First there is a need to embed in the mind of the patient a specific attitude about the test. Thus the patient is informed: "Dr. Reese realized that he was the expert on his visual needs, not his doctors. He was able to improve his own vision a great deal and others have also been helped by his method. If you can teach us exactly how you see, what works and doesn't work, maybe we can help you too. But you are the expert here. Our lenses and methods are useless without you doing your very best to tell us how you see and what makes things brighter, clearer, or more colorful and so on. Do you understand?. You are the expert here. You will lead the way if we are to help you. We hope so, but if we cannot, no harm is done. Are you ready? . . . Good, then let us begin."

The purpose of the foregoing is to eradicate a chronic sense of hopelessness that exists in many patients, that is that nothing can be done to help them. By associating the patient with the Dr. Reese story and telling him or her that he or she is the expert, hope for positive change is rekindled and motivation for the patient to communicate is encouraged. Patients tend to be submissive and intimidated by authorities. Immediate rapport with the doctor is achieved together with a sense of equality so the patient understands that he or she is an authority in the process.

The next step is for the practitioner to establish, for the patient, the meaning of "crisp, true clarity" in terms of the patient's vision. It is crucial that this be accomplished for optimal learning to occur. Otherwise the communications between the practitioner and the patient will be flawed.

The practitioner holds a small familiar object in his or her hand which may be a paper weight, a figurine or the like. Preferably it should be rich in color and have sharp clear lines. The practitioner holds the object against the white background of his or her coat and a reading lamp is positioned behind the patient's head to illuminate this coat in a bright manner with the light coming from over the patient's shoulder. The practitioner should be no more than two feet from the patient's eyes and the light should be at least 200 watts and both incandescent and fluorescent in order to approximate daylight conditions. The practitioner then hands the object to the patient and says, "Remember now you are the expert, hold this (whatever the object may be) and move it as close to your eyes (which are at the time uncorrected by any lens or the like) or as far away as required until this object and its details (which the practitioner may delineate) are as crystal clear to you as possible. Inform me specifically when you see it the very best that you can." In practice, each patient quickly finds a "near point of the best focus", usually quite close to the face, that is, two to five inches for vision-impaired people.

This individually selected "near point" is recorded precisely for each eye and with both eyes open.

With the foregoing information, the practitioner then announces to the patient "Now, when we begin working with the chart and using the lenses, I want you to remember exactly how clear things can be. Remember precisely how well you were able to see the object. You alone have this yardstick in your memory and in your feelings. Do you understand? . . . Good, you are the expert here so let us begin." This step of establishing from direct experience the patient's best clarity is crucial. It is something which the patient can only know and the practitioner must rely on the patient's use of that yardstick. No two vision patients are alike. The extent and location of retina scarring and damage vary from patient to patient. Incidentally, traditional methods implicitly rely broadly on the same type of yardstick but fail to teach and train low vision patients precisely what that yardstick is. It is essential that the patient be provided sufficient time to learn his or her best vision with the closely held object. Only the patient can determine this and this must never be forgotten in practicing the invention.

The next step involves the practitioner revealing the graphic of either FIG. 1, or preferably FIG. 2, and recording the patient's vision. In practice, it has been found best, however, to conduct a visual examination first by conventional means and a conventional graphic and then by using the graphic of FIGS. 1 or 2. Results from both are recorded. In the course of the examination using the graphic, the practitioner reminds the patient how clear things can be. "Near point" and "far point" are also recorded for both uncorrected and traditional corrections and also using the graphic of FIGS. 1 or 2.

After the foregoing has been concluded, which normally does not take more than ten or fifteen minutes, the practitioner commences using increasing power of the lenses and first uses an increase of at least 50%, that is 1.5 times the conventionally determined correction.

The patient is given a pencil flashlight or baton and is asked to look around the graphic and inform the practitioner exactly what he or she sees. The patient is again reminded that he or she is the only one who knows exactly what works and is the only one who knows the yardstick of what is crystal clear to him or her. The patient is instructed to point with the light or the baton at everything that he or she recognizes and to tell the practitioner what it is.

At this point in the process, if the patient has the potential to be improved significantly, it becomes almost immediately visible to the practitioner by the patient's increased excitement. The next twenty minutes to one-half hour are then devoted to the patient searching for optimal distance prescription by search for smaller and smaller symbols/numbers/letters on the graphic until a new prescription is reached, because no further improvement can be discovered. Every response on the patient's part is met with the practitioner reminding the patient of his or her sense of true clarity and at every juncture asking the patient to verify that same sense of true clarity experienced initially. When the practitioner and the patient believe that they have arrived at an optimal prescription, the object used to establish the yardstick of clarity is used again to compare "near point" distances by traditional means and using the new prescription. If the original distance was two inches, that distance will now be, say, ten inches with the prescription. This, in turn substantially improves the patient's distant vision for everyday living. The patient's perception of the extended world becomes much clearer and vivid which affords greater social mobility and an improved appearance of being normal.

During the period of working with the eye chart to determine the patient's best prescription, a marked improvement in focusing ability and a reduction of nystagmoid becomes clearly noticeable. The eye muscles are already learning to direct the eyes more precisely by the searching of the graphic and indeed, the practitioner's office itself may be used for this purpose. The real world environment is used indoors and outdoors periodically to confirm the findings provided by graphics during the testing process. In fact, it is this direct experience of improvement in functional mobility which determines the initial and final prescriptions. The multidirectional movement of the eyes with a motor commitment by the hands and the head as well as walking about the office and outside contribute to the learning process.

Once the practitioner, based on information from the patient, becomes certain that further changes in prescription lead to negligible changes and an optimal prescription has been ascertained, then he lets the patient rest and uses the retinoscope to assess the degree of neutralization which, in practice, has been found to be from good to excellent. These results are recorded.

The patient is then told the lenses will be ordered and when applied, vision training exercise will commence.

When the lenses arrive, the patient returns and is instructed in the exercises previously described and thereafter a weekly monitoring of changes in vision takes place. These monitoring sessions can be by the practitioner, a therapist or a trained assistant and the changes which take place are recorded.

Diagnoses for proper reading prescriptions are immediately made and patients are encouraged to experiment with various low vision aids and reading glasses.

Most changes required for reviewing prescriptions for the soft contact lenses occur within ten to thirty days. From experience obtained from patients in the clinical study, it is no longer believed necessary that six months to as much as one year of training is required. Nevertheless, weekly visits for one month are advise to be followed by visits of one per month for two months and finally once every three to six months thereafter.

When the patient's lenses are first applied, each patient is taught how to apply and remove his or her lenses. Extended wear soft contact lenses are used in almost all cases, if possible. Thus the patient need not handle the lenses every day. It has been found, as indicated above, that in most cases the final optimal prescription can be determined within one month after the lenses have been received and the exercises commenced.

In the training sessions the patients are encouraged to act autonomously and independently in the same manner as normally sighted people. They are encouraged to do as much as possible at the same distances which are used by normally sighted people so that they act and appear to others as normal.

The practitioner and therapist, who may be a psychologist or psychiatrist, observe the patients closely for neurotic, self-destructive, excessive dependencies upon the patient's parents or spouses inasmuch as this may require further psychotherapy so that the resulting autonomy gained by the patients from the process is not rejected. However, cases where further psychotherapy may be required seem, from the results of the clinical study, to be exceptional.

In addition, the professionals in charge of training sessions should caution the patients as they make progress against false hope and remind them that although their vision can be improved very substantially by the method, the damage to their retina will not be undone and the limitations caused thereby will remain. Therefore the patients are reminded that they must be realistic and, in particular, those who had at one time good vision must be informed that the same good vision cannot be restored by the method of the invention.

In addition to the improvements which occurred with the group in the clinical study related to above, reading speeds and ease of reading are improved in most cases and never have been diminished. Phobic fears such as anxiety and even panic in dealing with unfamiliar environments and conditions such as traffic, demanding social events and the like are radically reduced in most patients. Improvements are also substantial not only in the self-esteem, confidence and spontaneity of the patients but also in their grooming habits. Usually social and vocational improvements quite positive in nature are achieved.

It is to be understood that the procedures as set forth in the foregoing disclosure may be modified within limits depending upon the character of the vision impairment in the individual involved and whether the treatment is accorded to patients individually or in groups. Some features of the procedures can be employed without necessarily requiring a corresponding use of others. Accordingly, the following claims should be construed broadly in a manner consistent with the spirit and scope of the instant invention.

Having disclosed my invention, what I claim as novel and to be secured by Letters Patent of the United States is:

1. A method of determining optimal lens correction in a human subject suffereing from subnormal vision including severe myopia which comprises the subject wearing a soft contact lens of correction less than the estimated optimal correction for the subject and repeatedly on successive days testing with selected further lenses of different minus diopters in an outdoor, daytime environment to learn his or her best distance vision by selectively focusing on images at various distances while wearing said contact lenses, observing same through said contact lens and forward thereof a successively selected further spectacle lens until the best soft contact lens prescription for the subject's distance vision is ascertained from the combined correction of said contact lens and said spectacle lens which provides optimal lens correction for the subject.

2. A method in accordance with claim 1 wherein said subject also repeatedly on successive days tests the aforesaid contact lens and spectacle lens combinations indoors in a well illuminated area.

3. A method in accordance with claim 1 wherein said subject's head remains substantially stationary while said testing is performed.

4. The method of claim 1 wherein said subject is walking when said testing is performed.

5. A method in accordance with claim 1 wherein said subject is traveling in a vehicle when said testing is performed.

6. A method in accordance with claim 1 wherein the subject performs further reading test of his or her vision through said contact lenses at successively selected further plus diopter lens to determine his or her best correction for reading through spectacle lenses to be used with soft lenses of said optimal lens correction.

7. A method in accordance with claim 1 wherein supportive therapy is combined with said method.

8. A method in accordance with claim 7 wherein said supportive therapy comprises at least in part group therapy.

9. A method of determining optimal reading correction for a human subject suffering from subnormal vision including severe myopia which comprises the subject wearing a soft contact lens of a verified correction less than the estimated optimal correction for the subject and repeatedly testing on successive days with selected further lenses forward of said contact lens of different plus diopters for his or her best reading vision by reading while wearing said contact lenses through said contact lens and a successively selected one of said further spectacle lenses to determine the subject's best prescription for reading glasses to be used with further soft contact lenses which constitute the subject's optimal lens correction.

10. A method of determining optimal lens correction in a human subject suffering from subnormal vision including severe retina damage and focusing impairment which comprises the subject wearing a soft contact lens of correction of less diopter correction than the estimated optimal diopter correction of the subject and repeatedly on successive days testing with selected further lenses of different diopter magnitudes in an outdoor, daytime environment to learn his or her best distance vision by selectively focusing on images at various distances while wearing said contact lenses, observing same through said contact lens and forward thereof a successively selected further spectacle lens until the best soft contact lens prescription for the subject's distance vision is ascertained from the combined correction of said contact lens and said spectacle lens which provides optimal lens correction for the subject.

11. A method in accordance with claim 10 wherein said subject also repeatedly on successive days tests the aforesaid contact lens and spectacle lens combinations indoors in a well illuminated area.

12. A method in accordance with claim 10 wherein said subject is walking when said testing is performed.

13. A method in accordance with claim 10 wherein said subject is in a moving vehicle when said testing is performed.

14. A method in accordance with claim 13 wherein said subject's head remains substantially stationary while said testing is performed.

15. A method in accordance with claim 10 in combination with supportive therapy which ensures the subject knows what to expect in the method and for assisting the subject to overcome adverse reactions.

16. A method in accordance with claim 15 wherein at least part of said supportive therapy comprises group therapy.

* * * * *

UNITED STATES PATENT AND TRADEMARK OFFICE
CERTIFICATE OF CORRECTION

PATENT NO. : 4,979,812

DATED : December 25, 1990

INVENTOR(S) : Ronald E. Reese

It is certified that error appears in the above-identified patent and that said Letters Patent is hereby corrected as shown below:

On the title page, please insert:

--Related U. S. Application Data

Continuation-in-part of Ser.No. 558,047, Dec. 5, 1983, Pat.No. 4,747,682--

Signed and Sealed this

Twenty-first Day of September, 1993

Attest:

BRUCE LEHMAN

Attesting Officer

Commissioner of Patents and Trademarks